(12) United States Patent
Dai et al.

(10) Patent No.: US 6,429,336 B2
(45) Date of Patent: *Aug. 6, 2002

(54) PROCESS FOR RECOVERING TOLUENE DIAMINE FROM TOLUENE DIISOCYANATE DISTILLATION RESIDUES

(75) Inventors: Shenghong A. Dai, Lake Jackson; Duane S. Treybig, Sugarland; Kathryn Hock; Van A. Kent, both of Lake Jackson, all of TX (US)

(73) Assignee: The Dow Chemical Company, Midland, MI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/565,959

(22) Filed: May 5, 2000

Related U.S. Application Data

(60) Provisional application No. 60/132,544, filed on May 5, 1999.

(51) Int. Cl.⁷ .................... C07C 209/62; C07C 209/84; C07C 209/86
(52) U.S. Cl. ................ 564/414; 564/415; 564/437
(58) Field of Search ................ 564/414, 415, 564/437

(56) References Cited

U.S. PATENT DOCUMENTS

| | | | | |
|---|---|---|---|---|
| 3,128,310 A | * | 4/1964 | Koch | 564/414 |
| 3,225,094 A | * | 12/1965 | Wolf | 203/74 |
| 3,331,876 A | * | 7/1967 | Van Horn et al. | 564/414 |
| 3,499,035 A | * | 3/1970 | Kober et al. | 564/414 |
| 4,091,009 A | | 5/1978 | Cassata | |
| 4,137,266 A | | 1/1979 | Cassata | |
| 4,654,443 A | | 3/1987 | Marks et al. | |
| 4,843,108 A | | 6/1989 | Ruckes, et al. | |
| 4,970,342 A | | 11/1990 | Fauss, et al. | |

FOREIGN PATENT DOCUMENTS

| | | |
|---|---|---|
| EP | 0 219 035 A2 | 10/1986 |
| JP | 19740051942 | 5/1974 |
| JP | 54130525 | 9/1979 |
| JP | 54-130525 | 10/1979 |
| WO | WO 99/6568 | 12/1999 |

* cited by examiner

*Primary Examiner*—Brian J. Davis

(57) ABSTRACT

Residues from the distillation of a toluene diamine phosgenation mixture are hydrolyzed by mixing them with water and subjecting the mixture to a temperature of 200–350 ° C. The hydrolysis is performed in the presence of a sufficient amount of a base to maintain the pressure in the reactor to no more than a predetermined operating level. The product mixture is then extracted to recover TDA, which can be recycled. This provides an efficient process whereby nearly quantitative conversion of the residues to TDA can be achieved.

29 Claims, No Drawings

PROCESS FOR RECOVERING TOLUENE DIAMINE FROM TOLUENE DIISOCYANATE DISTILLATION RESIDUES

CROSS-REFERENCE TO RELATED APPLICATION

This application claims benefit under 35 USC §120 of U.S. Provisional Application No. 60/132,544 filed May 5,1999. That provisional application is hereby incorpoated by reference in its entirety.

BACKGROUND OF THE INVENTION

This invention relates to a process for recovering toluene diamine from toluene diisocyanate process residues. This invention particularly relates to hydrolysis of TDI distillation residues to toluene diamine.

Toluene diisocyanate (TDI) is commercially produced by phosgenating a toluene diamine (TDA) solution which is then distilled to produce a substantially pure TDI distillate and a process residue. The residue is a very complex mixture of high boiling materials and free TDI, which is commonly referred to as TDI Tar or TDI distillation residues.

The TDI distillation residues have no commercial value. As a result, these residues are usually disposed of. In order to try to reduce the waste from these residues, various attempts have been made to hydrolyze them and recover TDA. One such method is disclosed in U.S. Pat. No. 4,091,009 to Cassata ('009). In Cassata's process, TDI distillation residues are treated with aqueous ammonia or an alkaline earth to form a granular solid. While easier to handle than a tar-like material, the solids of this process likely have little value and must be further treated or disposed of in an economically and environmentally responsible manner.

Another process for disposing of TDI distillation residues is to hydrolyze them in the presence of aqueous ammonia as disclosed in U.S. Pat. No. 4,137,266, also to Cassata. In this reference, a granular solid such as that produced in '009, is heated in the presence of aqueous ammonia resulting in a recovery of about 60 to 70 percent of the solids as TDA. It is not always desirable to work with gaseous reactants such as ammonia.

Still another method for dealing with TDI distillation residues is disclosed in U.S. Pat. No. 4,654,443 to Marks et al. Marks describes treating TDI distillation residues by contacting them with a quantity of a polyamine to form a polyurea, and then hydrolyzing with water. A problem with this approach is that the additional step of adding a polyamine, even when all of that polyamine is recovered, requires that the polyamine go through the entire process, reducing the initial yield of the underlying TDI process and increasing equipment and energy required for handling the TDI distillation residues.

It would be desirable to provide an effective and relatively inexpensive method by which TDI distillation residues can be hydrolyzed to recover TDA in good yields.

SUMMARY OF THE INVENTION

In one aspect, this invention is a process for treating pumpable TDI distillation residues comprising a) forming a mixture of the TDI distillation residues and an excess of water, and b) maintaining said mixture in a closed reactor at a temperature of from about 200° C. to 350° C. for a period of time sufficient to hydrolyze at least 95% of the TDI distillation residues to TDA, wherein step b) is conducted in the presence of an amount of a strong base sufficient to maintain the pressure in the reactor to a predetermined level.

In another aspect, this invention is a process for treating pumpable TDI distillation residues, comprising a) forming a mixture of the TDI distillation residues and an excess of water, and b) maintaining said mixture in a closed reactor at a temperature of from about 200° C. to 350° C. for a period of time sufficient to hydrolyze at least 95% of the TDI distillation residues to TDA, c) during step b), monitoring the pressure in the reactor and d) if the pressure in the reactor exceeds a predetermined level, adding a sufficient amount of a strong base to reduce the pressure in the reactor to said predetermined level.

In a third aspect, this invention is a process for recovering TDA from TDI Tar comprising the steps of: (1) a first step (Step 1) of admixing fresh or stabilized TDI Tar with an aqueous basic solution in one or more vessels or reactors wherein the admixture is prepared by either: (a) first admixing the TDI Tar with the aqueous basic solution at a temperature of from about the melting point of the aqueous basic solution to about 200° C., with sufficient mixing so that the TDI Tar is converted to ureas, and then heating the admixture of ureas and aqueous basic solution to a temperature of from about 200° C. to 350° C.; or (b) admixing the tar with an aqueous basic solution at a temperature of from about 200° C. to about 350° C.; 2) a second step (Step 2) of maintaining the admixture of TDI Tar or ureas and aqueous basic solution at a temperature of from about 200° C. to 350° C. for a period of time sufficient to hydrolyze the ureas or TDI Tar to TDA wherein the pressure of the vessel or vessels or reactor or reactors is maintained at about the vapor pressure of water at the reaction temperature by (i) adding a sufficient initial quantity of base in Step (1) to absorb all or most of the carbon dioxide produced during the hydrolysis and (ii) adding as much additional base as necessary to maintain the pressure of the vessel or vessels or reactor or reactors at about the vapor pressure of water; (3) a third step (Step 3) of extracting TDA by admixing the crude TDA admixture from Step 2 with an organic solvent to produce a TDA and solvent extract and an aqueous raffinate; and (4) a fourth step (Step 4) of removing the solvent from the extract to produce TDA.

DESCRIPTION OF THE PREFERRED EMBODIMENTS

Residues from the distillation of a crude TDA phosgenation mixture are used as a starting material in this invention. These residues contain an amount of free toluene diisocyanate, along with higher boiling by-products of the phosgenation reaction. These by-products may include, for example, tarry TDI oligomers, ureas, urethanes, isocyanurates, biurets, allophanates, uretdiones, carbodiimides, urethane imines and other byproducts. Depending on how stringent the distillation conditions are (and to some extent the chlorine content), these by-products can advance in molecular weight to form an intractable, nonhydrolyzable mass. The starting material used in this invention is one that remains pumpable, which in the context of this invention means that the residue is a pumpable fluid at 160° C. TDI distillation residues typically remain pumpable if, during the distillation process, the free TDI content of the residues is not reduced below about 10% by weight. For purposes of overall efficiency of the TDI distillation process and subsequent hydrolysis according to this invention, TDI distillation residues having a free TDI content from about 12–30% by weight, preferably about 14–20% by weight, most preferably about 17–20%, by weight are preferred.

The TDI distillation residues are preferably used freshly from the distillation process, as a certain amount of undesirable molecular weight advancement occurs upon standing. However, it is possible to store the distillation residues for a period of time, especially if they have been stabilized. One process for stabilizing TDI residues is to pre-treat the fresh residues with enough of an aqueous basic solution to substantially prevent molecular weight advancement. Another process for stabilizing TDI distillation residues is to mix fresh residues with a solvent, which helps retard molecular weight advancement through simple dilution. The solvent is preferably one that is easily separated from the residues before conducting the hydrolysis or else does not react under the conditions of the hydrolysis reaction. Toluene is a preferred solvent. Toluene diisocyanate may also be used to dilute the distillation residues in order to stabilize them, but that is less preferred.

The TDI distillation residues are mixed with an excess of water, and said mixture is subjected to a temperature of from about 200° C. to 350° C. for a period of time sufficient to hydrolyze at least 95% of the TDI distillation residues to TDA Preferably, the conversion of residues to TDA is at least 98%, more preferably at least about 99% and most preferably at least 99.8%. An excess of water is used. Preferably at least about 5, more preferably at least about 6 parts of water are used per part by weight residues. The maximum amount of water is not critical, but excessive amounts of water do not provide any advantages and require larger and thus more expensive equipment. It is preferred to use less than about 20 parts water, and more preferred to use less than about 10 parts water, per part by weight residues.

If desired, the TDI distillation residues may be mixed with water at some temperature below 200° C., and the resulting mixture heated to 200° C. to 350° C. If the residues are mixed with water in this way, a preferred temperature is from about ambient to about 135° C., and a more preferred temperature is from about 35° C. to about 75° C. When the mixture is made at such lower temperatures, isocyanate groups in the residues will typically react with water to form ureas, which typically form a particulate dispersed in the aqueous phase. The mixture of residues and water is preferably agitated so that the urea forms fine particles suspended in excess water. The urea particles preferably are formed having an average diameter of less than 0.1 mm, more preferably less than 0.05 mm, and even more preferably less than 0.01 mm, in order to facilitate more rapid hydrolysis to TDA. The resulting suspension is then heated to a temperature of from about 200° C. to about 350° C. for a time sufficient to hydrolyze the particles to TDA. Preferably, the temperature of the hydrolysis reaction is above the melting temperature of the urea particles, i.e., above about 230° C. A more preferred temperature range is from about 230° C. to about 300° C., and a most preferred temperature range is from about 240° C. to about 270° C.

Alternatively, the residues can be mixed with water at the hydrolysis temperature, i.e., from about 200° C. to about 350° C., preferably from about 230° C. to about 300° C., and most preferably from about 240° C. to about 270° C.

The time required to hydrolyze the residues to TDA will vary as a function of the temperature and molecular weight of the TDI distillation residues being hydrolyzed. The lower the temperature used and the higher the molecular weight of the TDI distillation residues, the longer the time needed to fully hydrolyze the residues to TDA Typically, hydrolysis of 95% or more of the residues to TDA is accomplished within about 1 hour. It is more typically accomplished within about 15 minutes, and often within 10 minutes, at the most preferred temperature of about 240 to about 270° C.

The hydrolysis is performed in the presence of a strong base. The strong base is one that reacts with carbon dioxide to form a material that is liquid or solid at the temperature of the hydrolysis reaction. It is preferably one that accelerates hydrolysis reaction, as well. Preferred bases are alkali metal and alkaline earth hydroxides. Alkali metal hydroxides are more preferred, and sodium hydroxide and potassium hydroxide are most preferred. The amount of base that is used is sufficient to maintain the pressure in the hydrolysis reactor(s) to a predetermined level. Thus, in this invention, the addition of base is a important and sometimes a primary or even sole means of controlling process pressures to within a desirable range. Accordingly, this invention reduces or eliminates the need to vent the reactor in order to maintain pressure control. As a result, the loss of reactants such as TDA and water that often accompanies reactor venting can be reduced or eliminated. In addition, because reactor pressures are reduced, it is not necessary to construct the reactor to accommodate the higher pressures. As a result, less expensive reactors and associated equipment can be used.

Preferably, the amount of base that is used is sufficient to maintain the pressure in the reactor to no more than about 125% of the vapor pressure of water at the hydrolysis temperature. More preferably, the pressure is maintained at no more than 110% of the vapor pressure of water at the hydrolysis temperature. Even more preferably, the pressure is maintained at no more than about 105% of that of water and most preferably the pressure is maintained at no more than the vapor pressure of water at the hydrolysis temperature. Suitable operating pressures are from about 600 psi [4137 kPa], preferably from about 700 psi [4826 kPa], more preferably from 710 psi [4895 kPa], most preferably from about 720 psi [4964 kPa], to about 1000 psi [6895 kPa], preferably to about 900 psi [6205 kPa], more preferably to about 850 psi [5861 kPa], most preferably to about 800 [5516 kPa].

Although the invention is not to be limited by any theory, it is believed that the base limits pressure in the reactor by reacting with carbon dioxide to form water-soluble carbonate and bicarbonate salts. Carbon dioxide is generated by the hydrolysis of TDI Tar and this carbon dioxide, in a closed system, would significantly increase the pressure in the reactor. By reacting with the base, the gaseous carbon dioxide is thus eliminated from the headspace of the reactor, and thus does not contribute to the pressure inside of the reactor. Therefore, it is preferred to provide at least enough of the base to react with substantially all of the carbon dioxide that is generated in the hydrolysis reaction. amount of base required per a given quantity of residues will vary with the precise composition of the residues. In the operation of an industrial-scale TDI distillation unit, the composition of the residues tends to change over time. Thus, the precise amount of carbon dioxide that will be generated by hydrolyzing the residues may vary somewhat. In general, at least two equivalents of alkali metal hydroxide are used per NCO equivalent contained in the residues. Particularly suitable amounts of base are from about 2, preferably from about 7.5, more preferably from about 10 to about 50, preferably 30, more preferably to about 20, most preferably about 15 moles of base per kilogram of residues.

In addition to tying up carbon dioxide, the base, particularly alkali metal hydroxide, is believed to react with chlorine atoms in the residue to form water-soluble salts. Alkali metal hydroxides also provide an additional benefit of increasing the density of the aqueous phase, thereby simplifying the subsequent separation of the TDA from the water.

Thus, the amount of base is preferably selected together with the amount of water so the concentration of the base in the water is from about 6, preferably from about 6.5, most preferably from about 7 to about 10, preferably to about 9, and to about 8 percent by weight. When used at these concentrations, the salts produced in the hydrolysis reaction tend to stay in aqueous solution even if the solution is cooled substantially, for example, to 100° C., preferably to 80° C. or below, during subsequent filtering and/or extraction steps.

The base may all be added when the residues and water are first mixed together. Alternatively, the base may be fed into the mixture in two or more increments during the course of the hydrolysis reaction. If the residues and water are first mixed at temperatures below about 200° C., it is preferred that at least enough base be present in the initial mixture to react with the chlorine atoms in the residues. More preferably, most or all of the base that is required to control the reactor pressure is present when the residues are first mixed with the water.

In a highly preferred process, the pressure inside the reactor is monitored as the hydrolysis proceeds. If the pressure exceeds a predetermined level, base is added until the pressure is reduced to below that predetermined level.

Once the hydrolysis step is completed, the TDA is advantageously recovered from the reaction mixture. This is conveniently done by extracting the reaction mixture with an organic solvent to remove the TDA from the water. Preferably, the reaction mixture is cooled to below the boiling temperature (at atmospheric pressure) of the aqueous phase and organic solvent (but above the saturation point for the dissolved salts and by-products) before conducting the extraction. A preferred temperature is below about 100° C. a more preferred temperature is from about 70 to about 90° C. If any solids are present, they may be removed by any convenient solid-liquid separation technique, such as filtration or centrifugation, before the extraction is performed. Similarly, if some of the TDA has phase separated, it may be decanted or otherwise removed from the aqueous phase before the extraction is done. This allows the extraction to be performed with smaller volumes of materials, thereby reducing the capacity requirements of the extraction equipment.

The solvent used for the extraction of TDA is an organic solvent that (1) is immiscible in water, (2) is a better solvent for TDA than water is and (3) is a poorer solvent than water for the inorganic salts and other byproducts contained in the reaction mixture. Particularly suitable as solvents for the process of the present invention are aromatic hydrocarbons and ethers, chlorinated aromatic hydrocarbons and some ketones. Preferably, the solvent is toluene, dichlorobenzene, chlorobenzene, anisol, and mixtures thereof. Most preferably the organic solvent is anisole.

The TDA is advantageosly recovered from the extracting solvent. The method of doing this is not critical. One means of separating TDA from the solvent is recrystallization. A preferred method is distillation. The organic solvent removed from the product TDA can be recycled. If the extracting solvent/TDA mixture contains significant quantities of dissolved salts, it may be washed with water to remove them. The wash water can also be recycled into the process. For example, the wash water can be used to adjust the salt concentration of the aqueous phase of the reaction mixture before the extraction step.

If desired, the TDA may be purified further after it is recovered. Purification in this manner provides a further safeguard against contaminating TDA feed stocks when the recovered TDA is recycled into a TDI production process. A convenient purification method is distillation. Any residue from this step (or other steps) can be discarded.

The process of the present invention can be done batchwise or continuously. In either approach, the equipment used is selected to accommodate the pressures and environments of the process. For example, all vessels, reactors, exchangers and other equipment that is exposed to the aqueous basic solution of the process of the present invention is selected to be appropriate for being in contact with that solution under the reaction conditions of the process. One of ordinary skill in the art of conducting commercial scale chemical reactions such as the hydrolysis of TDI Tar to TDA will know how to select, size, assemble and operate the apparatus necessary to practice the process of the present invention. Particularly suitable equipment for the hydrolysis reaction includes continuous stirred tank reactors, tubular reactors, stirred tank reactors, and the like. For purposes of the present invention, the terms vessel and reactor are interchangeable and may include mixing by stirring or other forms of agitation even when the process of the present invention does not expressly require mixing. Also for purposes of the present invention, it is anticipated that the steps of process of the present invention can be performed in more that one vessel per step. For example, the hydrolysis step could be done in a series of 2 or more vessels.

The following examples are provided to illustrate the present invention. The examples are not intended to limit the scope of the present invention and should not be so interpreted. Amounts are in weight parts or weight percentages unless otherwise indicated.

EXAMPLE 1

51.3 ml/minute of a 7.5 percent aqueous solution of sodium hydroxide is fed into a 600 ml PARR* reactor equipped with an agitator (*PARR is a trade designation of Parr Instrument Company). Simultaneously, 7.6 ml/minute of a mixture TDI distillation residues containing about 14 percent TDI is fed into the 600 ml PARR reactor. The initial temperature of the sodium hydroxide solution is 180° C. and the initial temperature of the TDI Tar is 80° C. The PARR reactor is maintained at a temperature of about 265° C. and a pressure of about 750 psig [5171 kPa], or about 104% of the vapor pressure of water at that temperature. The residence time in the 600 ml PARR reactor is about 7 minutes after which the effluent from the 600 ml reactor flows into a second PARR Reactor having a capacity of 1 L and also held at a temperature of about 265° C. and a pressure of about 750 psig [5171 kPa]. The 1 L reactor is level controlled so that the reaction mixture has a residence time of 7 minutes in the second reactor. The effluent from this reactor is cooled to 80° C. and then extracted with anisole. The TDA/anisole extract is then distilled to remove the anisole. The product TDA is itself then distilled to insure purity.

The expected yield from these distillation residues, assuming 100% hydrolysis (i.e., assuming the residues contain no non-hydrolyzable species), is 63.5 grams per 100 grams of TDI distillation residues. 63 grams of TDA are recovered which corresponds to 99.2% conversion of distillation residues to TDA.

EXAMPLE 2

The process of Example 1 was substantially reproduced using a different batch of TDI distillation residues. In this case, the expected yield is about 64 grams per 100 grams residues 64 grams of TDA are recovered from 100 grams of the residues, which corresponds to essentially a 100% conversion of distillation residues to TDA.

What is claimed is:

1. A process for treating pumpable TDI distillation residues comprising
   a) forming a mixture of the TDI distillation residues and an excess of water, and
   b) maintaining said mixture in a closed reactor at a temperature of from about 200° C. to 350° C. for a period of time sufficient to hydrolyze at least 95% of the TDI distillation residues to TDA,
   wherein step b) is conducted in the presence of an amount of a strong base sufficient to maintain the pressure in the reactor at a predetermined level.

2. The process of claim 1 wherein said TDI distillation residues have a free TDI content of about 12 to about 30% by weight.

3. The process of claim 2 wherein said base is an alkali metal hydroxide.

4. The process of claim 3, wherein said temperature is from about 230° C. to about 300° C.

5. The process of claim 4, wherein the concentration of the alkali metal hydroxide in the water is from about 7 to about 10% by weight.

6. The process of claim 5 wherein said predetermined pressure is no greater than 110% of the vapor pressure of water at the temperature of the hydrolysis reaction.

7. The process of claim 5 which is operated as a continuous process.

8. The process of claim 5 which is operated batch-wise.

9. The process of claim 5 wherein TDA is recovered from the reaction by extraction with an organic solvent.

10. The process of claim 9 wherein TDA is recovered by separating it from the organic solvent.

11. A process for treating pumpable TDI distillation residues, comprising
    a) forming a mixture of the TDI distillation residues and an excess of water, and
    b) maintaining said mixture in a closed reactor at a temperature of from about 200° C. to 350° C. for a period of time sufficient to hydrolyze at least 95% of the TDI distillation residues to TDA,
    c) during step b), monitoring the pressure in the reactor and
    d) if the pressure in the reactor exceeds a predetermined level, adding a sufficient amount of a base to reduce the pressure to said predetermined level.

12. The process of claim 11 wherein said TDI distillation residues have a free TDI content of about 12 to about 30% by weight.

13. The process of claim 12 wherein said base is an alkali metal hydroxide.

14. The process of claim 13, wherein said temperature is from about 230° C. to about 300° C.

15. The process of claim 14, wherein the concentration of the alkali metal hydroxide in the water is from about 7 to about 10% by weight.

16. The process of claim 15 wherein said predetermined pressure is no greater than 110% of the vapor pressure of water at the temperature of the hydrolysis reaction.

17. The process of claim 15 which is operated as a continuous process.

18. The process of claim 15 which is operated batch-wise.

19. The process of claim 15 wherein TDA is recovered from the reaction by extraction with an organic solvent and TDA is recovered by separating it from the organic solvent.

20. A process for recovering TDA from TDI Tar comprising the steps of:
    (1) a first step of admixing fresh or stabilized TDI Tar with an aqueous basic solution in one or more vessels or reactors wherein the admixture is prepared by either:
        (a) first admixing the TDI Tar with the aqueous basic solution at a temperature of from about the melting point of the aqueous basic solution to about 200° C., with sufficient mixing so that the TDI Tar is converted to ureas, and then heating the admixture of ureas and aqueous basic solution to a temperature of from about 200° C. to 350° C.; or
        (b) admixing the TDI Tar with an aqueous basic solution at a temperature of from about 200° C. to about 350° C.;
    (2) a second step of maintaining the admixture of TDI Tar or ureas and aqueous basic solution at a temperature of from about 200° C. to 350° C. for a period of time sufficient to hydrolyze the ureas or TDI Tar to TDA wherein the pressure of the vessel or vessels or reactor or reactors is maintained at about the vapor pressure of water at the reaction temperature by
        (i) adding a sufficient initial quantity of base in Step (1) to absorb all or most of the carbon dioxide produced during the hydrolysis and
        (ii) adding as much additional base as necessary to maintain the pressure of the vessel or vessels or reactor or reactors at about the vapor pressure of water so that at least 95% of the TDI Tar admixed in Step (1) is hydrolyzed to TDA;
    (3) a third step of extracting TDA by admixing the crude TDA admixture from Step (2) with an organic solvent to produce a TDA and solvent extract and an aqueous raffinate; and
    (4) a fourth step of removing the solvent from the extract produce TDA.

21. The process of claim 20 wherein step (b) is carried out at a temperature of from about 230° C. to about 300° C. and pressure of at least 600 psi.

22. A process for treating pumpable TDI distillation residues comprising
    a) forming a mixture of the TDI distillation residues and an excess of water, and
    b) maintaining said mixture in a closed reactor at a temperature of from about 230° C. to about 300° C. for a period of time sufficient to hydrolyze at least 95% of the TDI distillation residues to TDA,
    wherein step b) is conducted in the presence of an amount of a strong base sufficient to maintain the pressure in the reactor at no more than 125% of the vapor pressure of water at the hydrolysis temperature, with the proviso that the hydrolysis is conducted at an operating pressure of at least 600 psi.

23. A process for treating pumpable TDI distillation residues comprising
    a) forming a mixture of the TDI distillation residues and an excess of water, and
    b) maintaining said mixture in a closed reactor at a temperature of from about 240° C. to about 270° C. for a period of time sufficient to hydrolyze at least 95% of the TDI distillation residues to TDA, wherein step b) is conducted at an operating pressure of from about 710 psi to about 850 psi in the presence of an amount of an alkali metal hydroxide sufficient to maintain the pressure in the reactor at a predetermined level.

24. The process of claim 9 wherein before conducting the extraction, the reaction mixture of step (b) is cooled to a temperature below the boiling temperature (at atmospheric pressure) of the aqueous phase and organic solvent but above the saturation point for any dissolved salts and byproducts in the reaction mixture, and wherein the solvent used for the extraction is toluene, dicholorobenzene, chlorobenzene, anisole, or a mixture thereof.

25. The process of claim 24 wherein the organic solvent is anisole and the extraction is carried out at a temperature of from about 70° C. to about 90° C.

26. The process of claim 20 wherein after step (2), but before step (3), the reaction mixture from step (2) is cooled to a temperature below about 100° C. but above the saturation point for any dissolved salts and byproducts in the reaction mixture, and wherein the organic solvent used in step (3) is selected from the group consisting of toluene, dichlorobenzene, chlorobenzene, anisole and mixtures thereof.

27. The process of claim 26 wherein the organic solvent is anisole and the extraction is carried out at a temperature of from about 70° C. to about 90° C.

28. The process of claim 23 wherein before conducting the extraction, the reaction mixture of step (b) is cooled to a temperature below the boiling temperature (at atmospheric pressure) of the aqueous phase and organic solvent but above the saturation point for any dissolved salts and byproducts in the reaction mixture, and wherein the solvent used for the extraction is toluene, dicholorobenzene, chlorobenzene, anisole, or a mixture thereof.

29. The process of claim 28 wherein the organic solvent is anisole and the extraction is carried out at a temperature of from about 70° C. to about 90° C.

* * * * *